(12) United States Patent
Chen et al.

(10) Patent No.: US 10,624,598 B2
(45) Date of Patent: Apr. 21, 2020

(54) SYSTEM AND METHOD FOR NAVIGATING A TOMOSYNTHESIS STACK INCLUDING AUTOMATIC FOCUSING

(71) Applicant: HOLOGIC, INC., Bedford, MA (US)

(72) Inventors: Jin-Long Chen, Santa Clara, CA (US); Haili Chui, Fremont, CA (US); Kevin Kreeger, Sunnyvale, CA (US); Xiangwei Zhang, Fremont, CA (US)

(73) Assignee: Hologic, Inc., Marlborough, MA (US)

( * ) Notice: Subject to any disclaimer, the term of this patent is extended or adjusted under 35 U.S.C. 154(b) by 614 days.

(21) Appl. No.: 14/771,696

(22) PCT Filed: Feb. 28, 2014

(86) PCT No.: PCT/US2014/019515
§ 371 (c)(1),
(2) Date: Aug. 31, 2015

(87) PCT Pub. No.: WO2014/149554
PCT Pub. Date: Sep. 25, 2014

(65) Prior Publication Data
US 2016/0051215 A1 Feb. 25, 2016

Related U.S. Application Data

(60) Provisional application No. 61/793,437, filed on Mar. 15, 2013.

(51) Int. Cl.
*G06K 9/00* (2006.01)
*A61B 6/00* (2006.01)
(Continued)

(52) U.S. Cl.
CPC .......... *A61B 6/5211* (2013.01); *A61B 6/025* (2013.01); *A61B 6/463* (2013.01); *A61B 6/469* (2013.01);
(Continued)

(58) Field of Classification Search
CPC ....... A61B 6/5211; A61B 6/025; A61B 6/463; A61B 6/469; A61B 6/502; A61B 6/5205;
(Continued)

(56) References Cited

U.S. PATENT DOCUMENTS 5,499,097 A   3/1996 Ortyn et al.
5,642,433 A   6/1997 Lee et al.
(Continued)

FOREIGN PATENT DOCUMENTS

WO   2005/110230    11/2005
WO   WO2013035026    3/2013
WO   2014/149554 A1   9/2014

OTHER PUBLICATIONS

PCT International Search Report for International Patent Appln. No. PCT/US2014/019515, Applicant Hologic, Inc., forms PCT/ISA/210 and 237, dated Aug. 26, 2014 (10 pages).
(Continued)

*Primary Examiner* — Vincent Rudolph
*Assistant Examiner* — Timothy Choi
(74) *Attorney, Agent, or Firm* — Vista IP Law Group, LLP (57) ABSTRACT

A system and method for reviewing a tomosynthesis image data set comprising volumetric image data of a breast, the method comprising, in one embodiment, causing an image or a series of images from the data set to be displayed on a display monitor and selecting or indicating through a user interface an object or region of interest in a presently displayed image of the data set, thereby causing an image from the data set having a best focus measure of the user selected or indicated object or region of interest to be automatically displayed on the display monitor.

4 Claims, 12 Drawing Sheets

(51) Int. Cl.

| | | |
|---|---|---|
| *A61B 6/02* | (2006.01) | |
| *G06F 3/0484* | (2013.01) | |
| *G06F 3/16* | (2006.01) | |
| *G06F 19/00* | (2018.01) | |
| *G06K 9/46* | (2006.01) | |
| *G06K 9/52* | (2006.01) | |
| *G06K 9/62* | (2006.01) | |
| *G06T 3/40* | (2006.01) | |
| *G06T 7/00* | (2017.01) | |
| *G06T 11/00* | (2006.01) | |
| *G06T 11/60* | (2006.01) | |

(52) U.S. Cl.
CPC .......... *A61B 6/502* (2013.01); *G06F 3/04842* (2013.01); *G06F 3/167* (2013.01); *G06F 19/321* (2013.01); *G06K 9/46* (2013.01); *G06K 9/4604* (2013.01); *G06K 9/4661* (2013.01); *G06K 9/52* (2013.01); *G06K 9/6201* (2013.01); *G06K 9/6267* (2013.01); *G06T 3/40* (2013.01); *G06T 7/0012* (2013.01); *G06T 11/001* (2013.01); *G06T 11/60* (2013.01); *A61B 6/5205* (2013.01); *G06K 2009/4666* (2013.01); *G06T 2207/10112* (2013.01); *G06T 2207/30068* (2013.01); *G06T 2207/30168* (2013.01)

(58) Field of Classification Search
CPC .... G06F 3/04842; G06F 3/167; G06F 19/321; G06K 9/46; G06K 9/44604; G06K 9/4661; G06K 9/52; G06K 9/6201; G06K 9/6267; G06K 2009/4666; G06T 3/40; G06T 7/0012; G06T 11/001; G06T 11/60; G06T 2207/10112; G06T 2207/30068; G06T 2207/30168; G06T 2207/20101; G06T 2207/20104; G06T 2207/201
See application file for complete search history.

(56) References Cited

U.S. PATENT DOCUMENTS

| | | | |
|---|---|---|---|
| 5,642,441 | A | 6/1997 | Riley et al. |
| 5,647,025 | A | 7/1997 | Frost et al. |
| 5,671,288 | A | 9/1997 | Wilhelm et al. |
| 5,763,871 | A | 6/1998 | Ortyn et al. |
| 5,841,124 | A | 11/1998 | Ortyn et al. |
| 5,875,258 | A | 2/1999 | Ortyn et al. |
| 6,215,892 | B1 | 4/2001 | Douglass et al. |
| 6,327,377 | B1 | 12/2001 | Rutenberg et al. |
| 7,117,098 | B1 | 10/2006 | Dunlay et al. |
| 7,630,533 | B2 * | 12/2009 | Ruth ............... G06K 9/4638 382/131 |
| 7,769,219 | B2 * | 8/2010 | Zahniser ............. G02B 21/244 348/356 |
| 2005/0047636 | A1 | 3/2005 | Gines et al. |
| 2007/0225600 | A1 | 9/2007 | Weibrecht et al. |
| 2009/0087067 | A1 | 4/2009 | Khorasani |
| 2011/0110576 | A1 * | 5/2011 | Kreeger ............. G06F 19/3406 382/132 |
| 2011/0150447 | A1 * | 6/2011 | Li ..................... H04N 5/23212 396/104 |
| 2014/0219534 | A1 * | 8/2014 | Wiemker ............ G06T 7/0012 382/131 |

OTHER PUBLICATIONS

Response to Rule 161(1) and 162 communication filed on Jun. 6, 2016 for European Patent Application No. 14711087.8, 14 pages.
EPO office action dated Feb. 5, 2018 for European Patent Application No. 14711087.8, 4 pages.
Response to EPO office action filed on Aug. 9, 2018 for European Patent Application No. 14711087.8, 6 pages.
Chinese office action dated Mar. 1, 2018 for Chinese Patent Application No. 201480014655.2, in Chinese with English translation provided by Chinese associate, 18 pages.
Chinese office action dated Sep. 18, 2018 for Chinese Patent Application No. 201480014655.2, in Chinese with English translation provided by Chinese associate, 27 pages.
Chinese office action dated Apr. 16, 2019 for Chinese Patent Application No. 201480014655.2, in Chinese with English translation provided by Chinese associate, 27 pages.
First office action for Japanese Application No. 2016-200514 dated Dec. 11, 2017, including English translation provided by foreign associate, 12 pages.
Response to first office action filed Mar. 12, 2018 for Japanese Application No. 2016-200514, including English translation provided by foreign associate, 41 pages.
Response to third office action filed on Sep. 2, 2019 for Chinese Application No. 201480014655.2, in Chinese with partial translation provided by foreign associate, 23 pages.
Notification of the International Preliminary Report on Patentability dated Sep. 24, 2015 for PCT/US2014/019515, 8 pages.

* cited by examiner

SYSTEM AND METHOD FOR NAVIGATING A TOMOSYNTHESIS STACK INCLUDING AUTOMATIC FOCUSING

RELATED APPLICATION DATA

The present application is a National Phase entry under 35 U.S.C § 371 of International Patent Application No. PCT/US2014/019515, having an international filing date of Feb. 28, 2014, which claims the benefit under 35 U.S.C. § 119 to U.S. Provisional Patent Application Ser. No. 61/793,437, filed Mar. 15, 2013, which is incorporated by reference in its entirety into the present application.

FIELD

The inventions disclosed herein pertain to breast imaging using tomosynthesis, and more specifically to a system and method that employs automated focusing capabilities for guiding the navigation of a tomosynthesis data set.

BACKGROUND

Mammography has long been used to screen for breast cancer and other abnormalities. Traditionally, mammograms have been formed on x-ray film. More recently, flat panel digital imagers have been introduced that acquire a mammogram in digital form, and thereby facilitate analysis and storage of the acquired images, and provide other benefits as well. Further, substantial attention and technological development has been dedicated towards obtaining three-dimensional images of the breast, using methods such as breast tomosynthesis. In contrast to the 2D images generated by legacy mammography systems, breast tomosynthesis systems construct a 3D image volume from a series of 2D projection images, each projection image obtained at a different angular displacement of an x-ray source relative to the image detector as the x-ray source is scanned over the detector. The constructed 3D image volume is typically presented as a plurality of slices of image data, the slices often being geometrically reconstructed on planes parallel to the paddle, although other reconstruction angles are possible. The reconstructed tomosynthesis slices reduce or eliminate the problems caused by tissue overlap and structure noise present in single projection 2D mammography imaging, by permitting a reviewer (e.g., a radiologist or other medical professional) to scroll through the image slices to view underlying structures.

Tomosynthesis systems have recently been developed for breast cancer screening and diagnosis. In particular, Hologic, Inc. (www.hologic.com), has developed a fused, multimode mammography/tomosynthesis system that acquires one or both types of mammogram and tomosynthesis images, either while the breast remains immobilized or in different compressions of the breast. Other companies have proposed the introduction of systems which are dedicated to tomosynthesis imaging only, i.e., which do not include the ability to also acquire a 2D mammogram.

However, systems restricted to tomosynthesis acquisition and image display are slow to gain acceptance as a replacement for conventional 2D mammogram images. In particular, conventional 2D mammograms provide good visualization of micro-calcifications, and can offer higher spatial resolution, when compared with tomosynthesis images. While tomosynthesis images provided by dedicated breast tomosynthesis systems have many desirable characteristics, e.g., better isolation and visualization of structures in the breast, such systems do not necessarily leverage existing image interpretation expertise.

In particular, because of the limited angle employed during tomosynthesis image acquisition, a breast structure would normally be visible on multiple tomosynthesis reconstructed image slices. However, it is only near the actual "depth" (location along the z-axis of the tomosynthesis images) where the breast structure is actually located that the image slices for that structure will provide sharp margin/contour/detail of the structure, i.e., as if the structure/object is "in-focus"; whereas on other slices, the structure/object may be visible but associated with fuzzy margin/contour/detail, i.e., as if the structure/object is "out-of-focus." Further, it is possible that some objects or regions of interest will only be recognizable in image slices that are reasonably close to the actual object/structure depth. As such, a reviewer may need to expend a relatively significant amount of time navigating through the images of the entire breast tomosynthesis stack, which can typically include 40-100 images, or more, depending on the breast size and reconstruction slice thickness, in order to locate a "best focus" image of an object or region of clinical interest for purposes of evaluation. This additional time needed to review a tomosynthesis stack can detour the reviewer from otherwise taking full advantage of the additional benefits provided by detailed tomosynthesis image slices over a traditional mammogram, especially when given the limited amount of time typically allocated for the review.

Thus, it would be of particular benefit to provide a system and methods for providing the reviewer with the ability to quickly and accurately locate an image or subset of images having a best focus of an object or region of interest in a tomosynthesis stack.

SUMMARY

According to one aspect of the inventions disclosed and described herein, a computer-controlled workstation is provided for navigating and reviewing a tomosynthesis image data set, the data set comprising volumetric image data of a breast, wherein the workstation is configured to display an image or a series of images from the data set on a display monitor operatively associated with the workstation, and wherein a reviewer may select or otherwise indicate through a user interface of the system an object or region of interest in a presently displayed image of the data set, thereby causing to be automatically displayed on the display monitor an image from the data set having a best focus measure of the user selected or indicated object or region of interest. Additionally and/or alternatively, in response to a detected user selection or indication of an object or region of interest in a then-displayed image from the data set, the system displays a series of near-focus images from the data set, the series comprising images having computed focus measure values within a predetermined range of, and including, a best focus measure value computed for any image of the data set depicting the user selected or indicated object or region of interest. In either case, if the then-displayed image comprises the image having the best focus of the user selected or indicated object or region of interest, the workstation may provide a visual or audible signal to the user.

In particular, because of the limited angle employed during tomosynthesis image acquisition, a breast structure would normally be visible on multiple tomosynthesis reconstructed image slices. However, it is only near the actual "depth" (location along the z-axis of the tomosynthesis images) that the breast structure is actually located that the image slices for that structure will provide sharp margin/contour/detail of the structure, i.e., as if the structure/object is "in-focus"; whereas on other slices, the structure/object may be visible but associated with fuzzy margin/contour/detail, i.e., as if the structure/object is "out-of-focus." Further, it is possible that some objects or regions of interest will only be recognizable in image slices that are reasonably close to the actual object/structure depth. As such, without the advantages provided by the inventions disclosed herein, a reviewer may need to expend a relatively significant amount of time navigating through the images of an entire breast tomosynthesis stack, which can typically include 40-100 images, or even more, depending on the breast size and reconstruction slice thickness, in order to locate a "best focus" image of an object or region of clinical interest for purposes of evaluation. Thus, it is of particular benefit of the disclosed inventions to provide a system and methods for providing the reviewer with the ability to quickly and accurately locate an image or subset of images having a "best focus" of an object or region of interest in a tomosynthesis stack.

In various embodiments of the disclosed invention, the image having a best focus measure of the user selected or indicated object or region of interest is determined based on a comparison of a focus measure of the object or region of interest computed for each image of the data set. By way of non-limiting examples, the focus measure may be computed based upon a sharpness of detected edges of the object or region of interest, a contrast of the object or region of interest, or a ratio between a measured magnitude of one or more high frequency components and a measured magnitude of one or more low frequency components. It follows that a subset of near-focus images may be identified based on their proximity in the tomosynthesis stack, i.e., along the z-axis of the images, to the image having a highest focus measure.

In some embodiments, the user selected or indicated object or region of interest may be highlighted in the displayed image having a best focus thereof. For example, the user selected or indicated object or region of interest may be highlighted by a contour line representing a boundary of the highlighted object or region. Additionally and/or alternatively, the user selected or indicated object or region of interest is highlighted in a manner indicating that the highlighted object or region is or includes a specified type of tissue structure.

In embodiments in which the system displays a series of near-focus images in response to detecting a user selection or indication of an object or region of interest, the series of near-focus images may be displayed simultaneously, i.e., in a particular order, so as to allow for a static review and comparison of the user selected or indicated object or region of interest in each image. Alternatively and/or additionally, the series of near-focus images may be displayed in succession, so as to allow for a dynamic review and comparison of the user selected or indicated object or region of interest in each image. For example, the parameters for the selection and displaying of the series near-focus images may be configurable through the user interface. In one embodiment, the series of near-focus images are displayed one-by-one, starting from a farthest from focused image, and thereafter continually approaching, and (optionally) ending with, the best focus image. Once the best focus image is reached, instead of ending the display sequence, the system may (e.g., based on a user preference) display the next adjacent near focus images, up to a certain range, then come back to the best focus image, thereby allowing the user to get a good perspective of all the images surrounding the best focus image.

In accordance with another embodiment of the disclosed inventions, an automated method employing a computer-controlled workstation is provided for navigating and displaying breast tissue images, the workstation comprising an operatively associated user interface and display monitor, the method comprising: obtaining a tomosynthesis image data set, the data set comprising volumetric image data of a breast; displaying a series of images from the data set on the display monitor in response to one or more user commands received through the user interface; detecting through the user interface a user selection or indication of an object or region of interest in a then-displayed image from the data set; highlighting the user selected or indicated object or region of interest in the then-displayed image with a visual indicia; and as further images of the series are displayed, continuing to highlight the user selected or indicated object or region of interest, while modifying the visual indicia.

The visual indicia may be a geometric shape, wherein modifying the visual indicia comprises changing a size of the geometric shape according to a relative focus measure of the user selected or indicated object or region of interest in a currently displayed image. Alternatively, the visual indicia may be a color, wherein modifying the visual indicia comprises changing a hue of the color according to a relative focus measure of the user selected or indicated object or region of interest in a currently displayed image.

These and other aspects and embodiments of the disclosed inventions are described in more detail below, in conjunction with the accompanying figures.

DETAILED DESCRIPTION OF THE ILLUSTRATED EMBODIMENTS

In describing the depicted embodiments of the disclosed inventions illustrated in the accompanying figures, specific terminology is employed for the sake of clarity and ease of description. However, the disclosure of this patent specification is not intended to be limited to the specific terminology so selected, and it is to be understood that each specific element includes all technical equivalents that operate in a similar manner. It is to be further understood that the various elements and/or features of different illustrative embodiments may be combined with each other and/or substituted for each other wherever possible within the scope of this disclosure and the appended claims.

Tomosynthesis Imaging Acquisition and Computation

Figure 1:
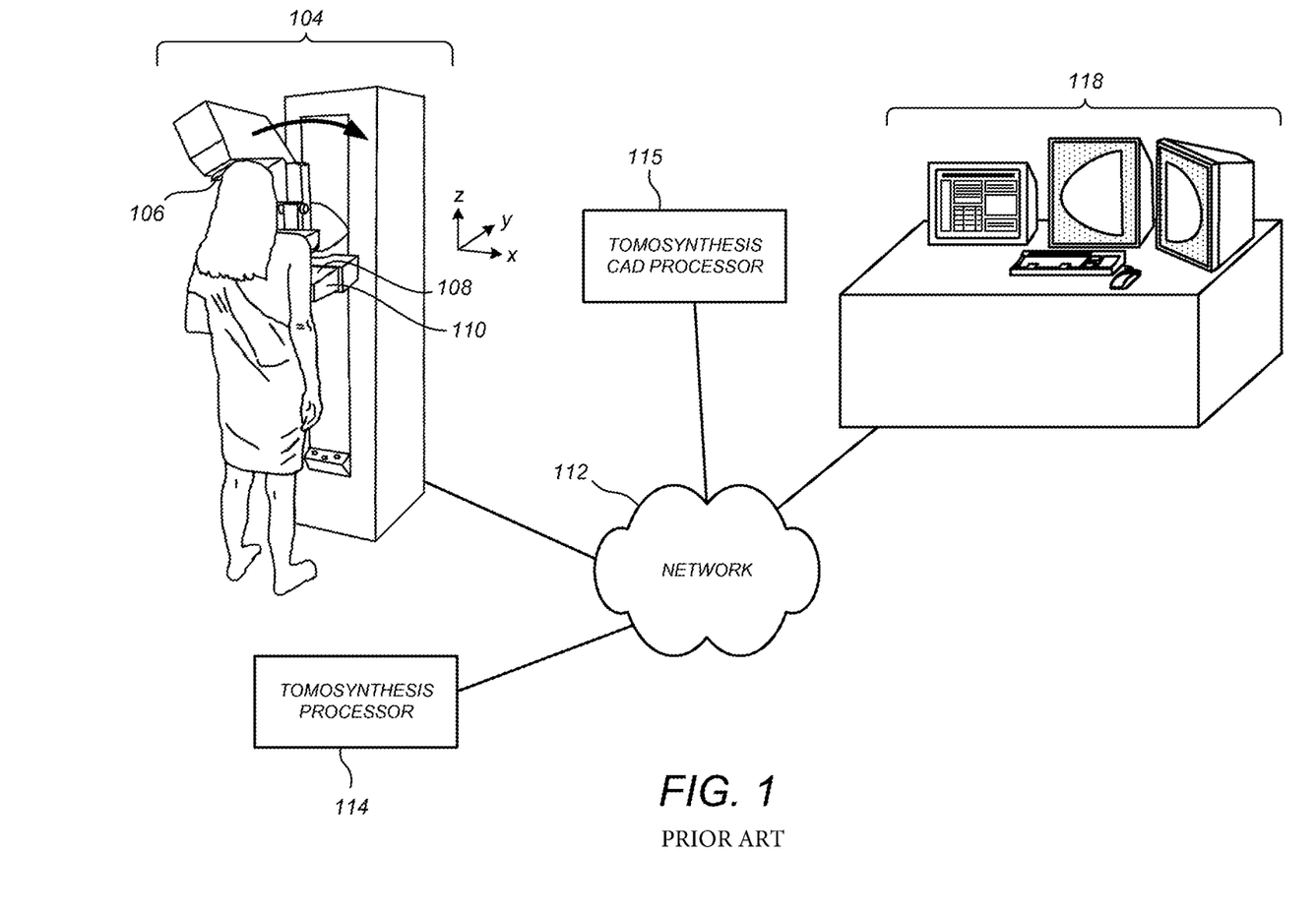
FIG. 1 illustrates a conceptual diagram of a breast x-ray tomosynthesis imaging environment, including a tomosynthesis CAD processor.
Figure 2:
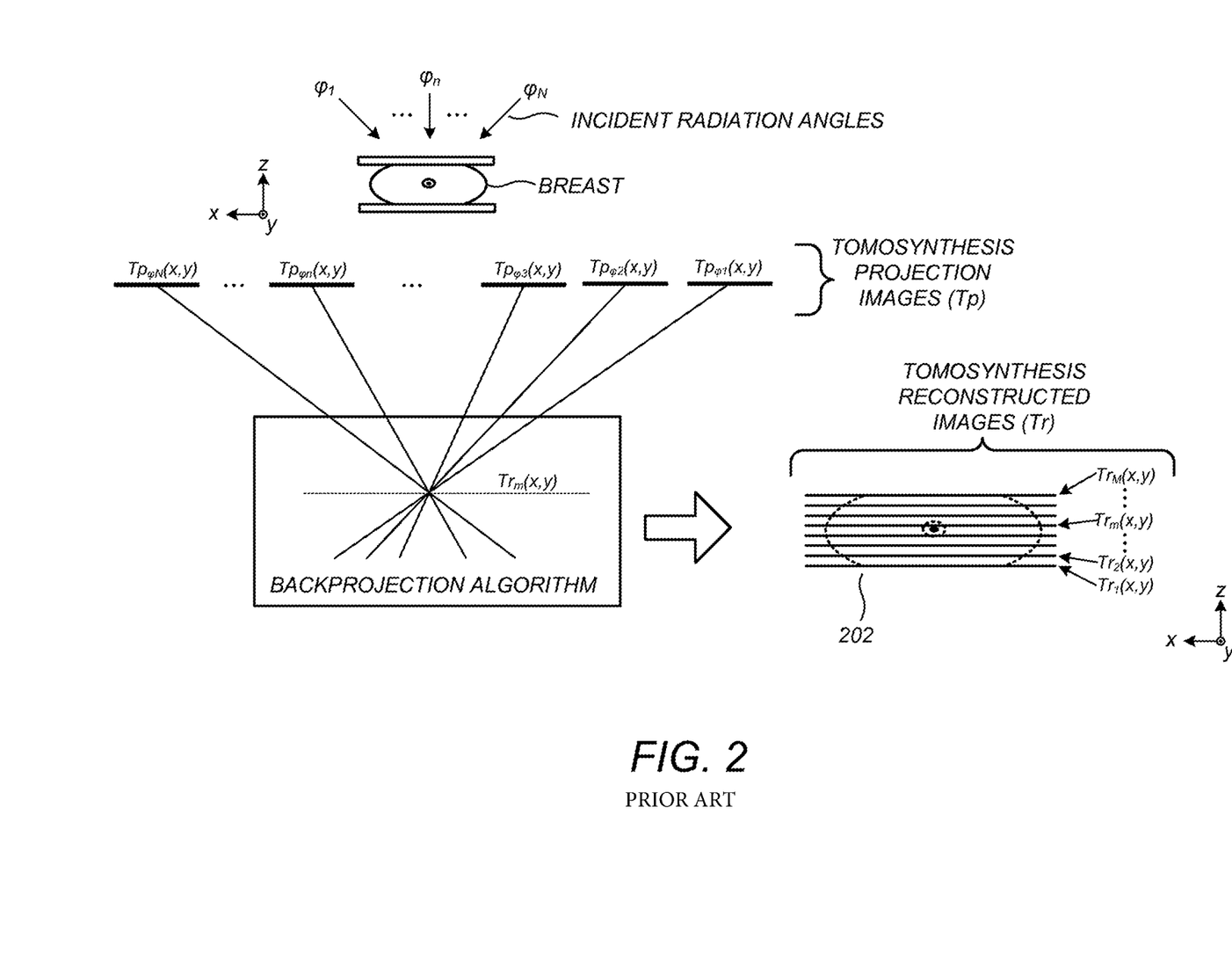
FIG. 2 illustrates exemplary breast x-ray tomosynthesis projection and reconstruction geometries.

In order to provide additional background information, reference is made to FIG. 1 and FIG. 2 taken from U.S. Pat. No. 8,223,916, entitled "Computer-aided detection of anatomical abnormalities in x-ray tomosynthesis images," which is incorporated herein by reference in its entirety.

FIG. 1 illustrates a conceptual diagram of a breast x-ray tomosynthesis imaging environment, including Computer Aided Detection (CAD) capability. Shown in FIG. 1 is a network 112, which may be a HIS/RIS (Hospital Information System/Radiology Information System) network, to which is coupled a breast x-ray tomosynthesis acquisition device 104. The acquisition device 104 includes an x-ray source 106 projecting x-rays toward a woman's breast that is supported on a breast platform 108, along with an x-ray imager 110 underlying the breast platform 108. The x-ray source 106 is moved in an arcuate path relative to the breast platform 108 and emits x-ray radiation at specified angles therealong which are captured by the x-ray imager 110 to form a set of tomosynthesis projection images. The tomosynthesis projection images are processed by a tomosynthesis processor 114 according to one or more tomosynthesis reconstruction algorithms to form tomosynthesis reconstructed images, these images being formed and filtered with a view toward optimal visual display to a radiologist ("for presentation"). In a separate process, the tomosynthesis projection images are processed by a tomosynthesis CAD processor 115 to detect anatomical abnormalities in the breast volume. The tomosynthesis image information is then viewed in conjunction with the associated CAD results at a radiology review workstation 118.

FIG. 2 illustrates a conceptual diagram of breast x-ray tomosynthesis projection imaging at different angles. Incident radiation impinges upon a compressed breast volume at a plurality "N" of breast x-ray tomosynthesis projection angles $\varphi_n$=1 ... N, to result in a corresponding plurality "N" of tomosynthesis projection images $Tp_{\varphi n}(x,y)$, n=1 ... N. In typical scenarios, there can be N=11 or N=15 projection images, each projection image $Tp_{\varphi n}(x,y)$ containing roughly 1710×2140 pixels, which would correspond to an x-ray detector that is roughly 24 cm×30 cm in size having a pixel resolution of 140 μm.

Also illustrated in FIG. 2 is a three-dimensional geometry 202 for the imaged breast volume, along with a conceptual icon of a tomosynthesis reconstruction algorithm in which, for a particular plane "m" having a predetermined height $h_m$, above the detection plane, the "N" projection images $Tp_{\varphi n}(x,y)$, n=1 ... N, are processed into a two-dimensional tomosynthesis reconstructed image $Tr_m(x,y)$. More specifically, the N projection images $Tp_{\varphi n}(x,y)$, n=1 ... N are combined by backprojection (or other tomosynthesis reconstruction algorithm) to form the tomosynthesis reconstructed image $Tr_m(x,y)$ based on that specific value of $h_m$ in a manner that highlights (e.g., does not blur) the effects of x-ray attenuating tissues located near that predetermined height $h_m$ and that de-emphasizes (e.g., blurs) x-ray attenuating tissues located away from that predetermined height $h_m$.

In theory, the number of different predetermined heights $h_m$ for which distinct two-dimensional tomosynthesis reconstructed images $Tr_m(x,y)$ can be generated is arbitrarily large, because $h_m$ is simply a selectable parameter fed to the reconstruction (backprojection) algorithm. In practice, because the ultimate amount of useful information is limited by the finite count of "N" projection images, the tomosynthesis reconstruction geometry is usually limited to a predetermined number "M" of reconstructed image arrays $Tr_m(x,y)$. Preferably, the number "M" is selected such that the reconstructed image arrays $Tr_m(x,y)$ uniformly fill out the vertical extent of the imaged breast volume between the lower and upper compression plates, at a vertical spacing (such as 1 mm) that is small enough to capture smaller-sized micro-calcifications.

The lateral extent of each tomosynthesis reconstruction image $Tr_m(x,y)$, can be similar to that of each projection image $Tp_{\varphi n}(x,y)$, i.e., the number of pixels and the spatial resolution of the tomosynthesis reconstructed images $Tr_m(x,y)$ can be similar as for the projection images $Tp_{\varphi n}(x,y)$. However, such correspondence is not required, with supersampling, subsampling, or other resampling being available for various reasons. For example, the particular geometries of different tomosynthesis reconstruction algorithms could be different from each other, in which case such resampling is incorporated therein as needed to cause the resultant arrays that will be being compared, added, multiplied, mapped, or otherwise jointly processed to be in registration with each other. Depending on the particular tomosynthesis reconstruction algorithm being used, the lateral resolution of the different tomosynthesis reconstructed images $Tr_m(x,y)$ can be different for different levels, for example, the uppermost level could be 95 μm per pixel while the lowermost level be 108 μm per pixel.

As used herein, three-dimensional geometry of the imaged breast volume refers to a space-limited three-dimensional grid having a defined number of levels that extends at least throughout a clinically relevant portion of the breast (for example, including the breast parenchyma but excluding the skin and the empty space around the breast between the compression plates). In the event only a single predefined tomosynthesis reconstruction algorithm is involved, the three-dimensional geometry of the imaged breast volume can be based upon the number of levels in that predefined tomosynthesis reconstruction algorithm. In the event multiple predefined tomosynthesis reconstruction algorithms are involved having different geometries, the three-dimensional geometry of the imaged breast volume can be based on one of them, with resampling being incorporated into the others to result in appropriate registration. Alternatively, the three-dimensional geometry of the imaged breast volume could be based on the tomosynthesis reconstruction algorithms that were, or will be, used to generate the "for presentation" tomosynthesis reconstructed images.

Navigation and Review of Displayed Tomosynthesis Image Set.

Preferred embodiments of a tomosynthesis workstation employing an automated focus capability according to the presently disclosed inventions will now be described. It is to be appreciated by those skilled in the art that the particular components of the review workstation are described in a very basic (generic) fashion, and that the inventions disclosed herein may be practiced on any of a wide number, type and variety of computer (processor) controlled workstations, which are common place as of this time. As used herein, the terms "user" and "reviewer" are intended to be used interchangeably.

In particular, an exemplary system for navigating and reviewing a tomosynthesis image data set includes an image processor (e.g., a computer), an image display monitor operatively associated with the image processor; and a user interface operatively coupled to the image processor and display monitor, wherein the user interface may in fact comprise in whole or part the display monitor (i.e., in a touch screen device such as a "tablet", "pod" or other "smart" device). The image processor is configured to display user-selected image slices from a tomosynthesis data set on the display monitor in response to one or more user commands received through the user interface. The image processor is further configured to detect through the user interface a user selection or indication of an object or region of interest in a then-displayed image from the data set (e.g., when the user positions a graphic arrow controlled by a "mouse device" over the respective object or region for a certain amount of time and/or affirmative actuates (e.g., by clicking) same while in that position.

Figure 3:
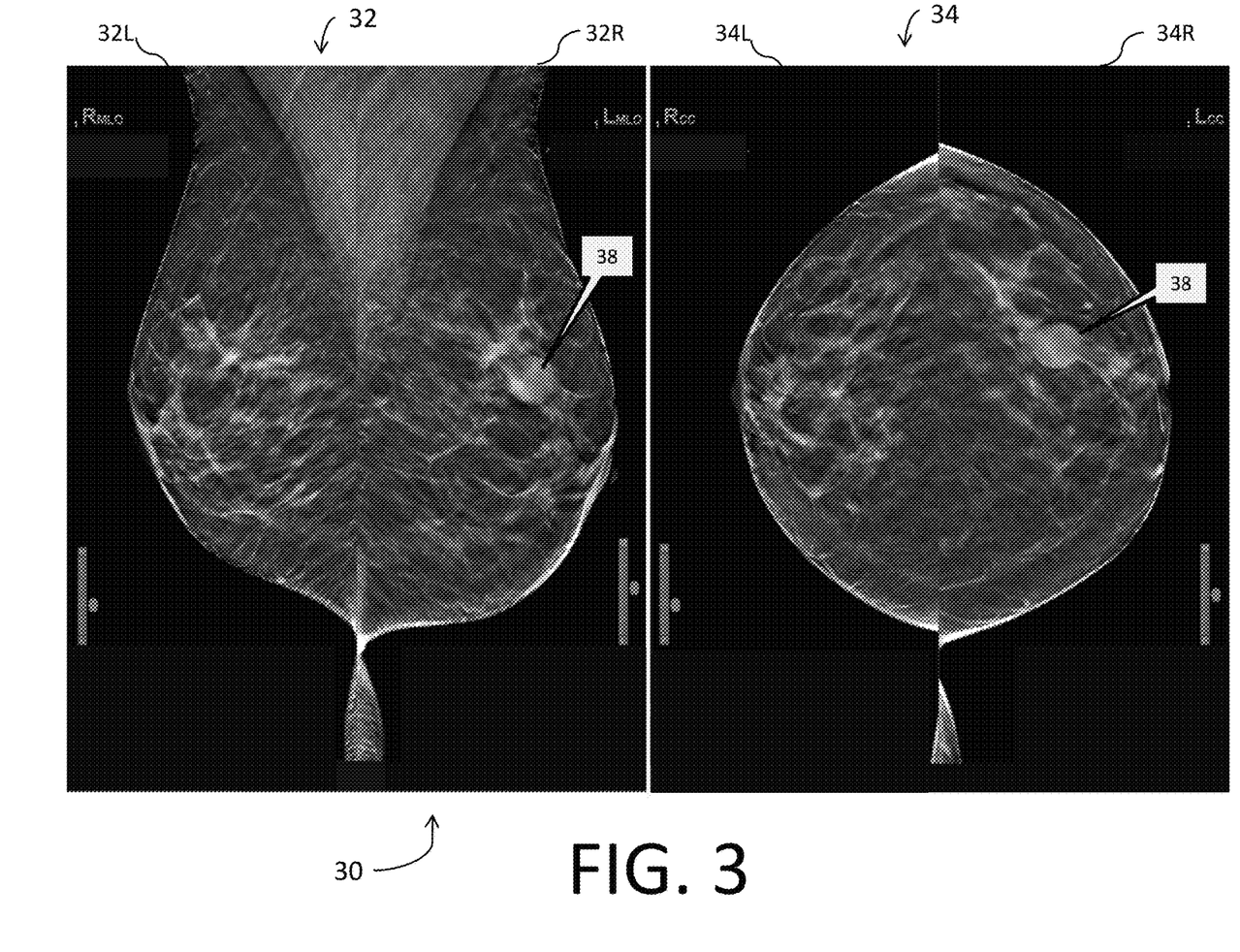
FIG. 3 depicts adjacent display monitors of an exemplary tomosynthesis image review workstation, including a left-hand monitor displaying respective $R_{MLO}$ and $L_{MLO}$ image slices; and a right-hand monitor displaying respective $R_{CC}$ and $L_{CC}$ image slices.

For purposes of more specific illustration, FIG. 3 depicts adjacent display monitors 32 and 34 of an exemplary tomosynthesis image review workstation 30, including a left-hand monitor 32 displaying respective right and left mediolateral oblique ("$R_{MLO}$" and "$L_{MLO}$") image slices 32L and 32R; and a right-hand monitor 34 displaying respective right and left craniocaudal ("$R_{CC}$" and "$L_{CC}$") image slices 34L and 34R. The $R_{MLO}$, $L_{MLO}$, $R_{CC}$, and $L_{CC}$ images are obtained from respective tomosynthesis image sets ("tomo stacks") containing right and left breast image data for each of the mediolateral oblique and craniocaudal orientations, for a total of four different tomo stacks. In particular, the displayed $R_{MLO}$ view is image 18 out of a 48 slice $R_{MLO}$ tomo stack; the displayed $L_{MLO}$ view is image 28 out of a 48 slice $L_{MLO}$ tomo stack; the displayed $R_{CC}$ view is image 18 out of a 48 slice $R_{CC}$ tomo stack; and the displayed $L_{CC}$ view is image 24 out of a 48 slice $L_{MLO}$ tomo stack. It will be appreciated by those skilled in the art that different tomo stacks may comprise differing numbers of image slices, and that the example tomo stacks having 48 image slices each are merely for example.

Notably, a round tissue mass 38 is visible in each of the $L_{MLO}$ and $L_{CC}$ image slices. It will be appreciated that the particular views of the tissue mass in the respective $L_{MLO}$ and $L_{CC}$ image slices differ in both clarity and orientation, since the image slices are taken along different (orthogonal) image planes, i.e., with the $L_{MLO}$ slice 28 comprising a cross-section taken along the z-axis of a "side view", and the $L_{CC}$ slice 24 comprising a cross-section taken along the z-axis of a top-down view that is orthogonal to the z-axis of the $L_{MLO}$ image set.

For purposes of simplifying the discussion, the remainder of the present specification refers just to the $L_{CC}$ (left breast craniocaudal) tomo stack, although the inventive concepts and features described apply equally to the navigation and review of any tomo image stack, as well as for other, non-breast, body tissue image volumes.

Figure 4:
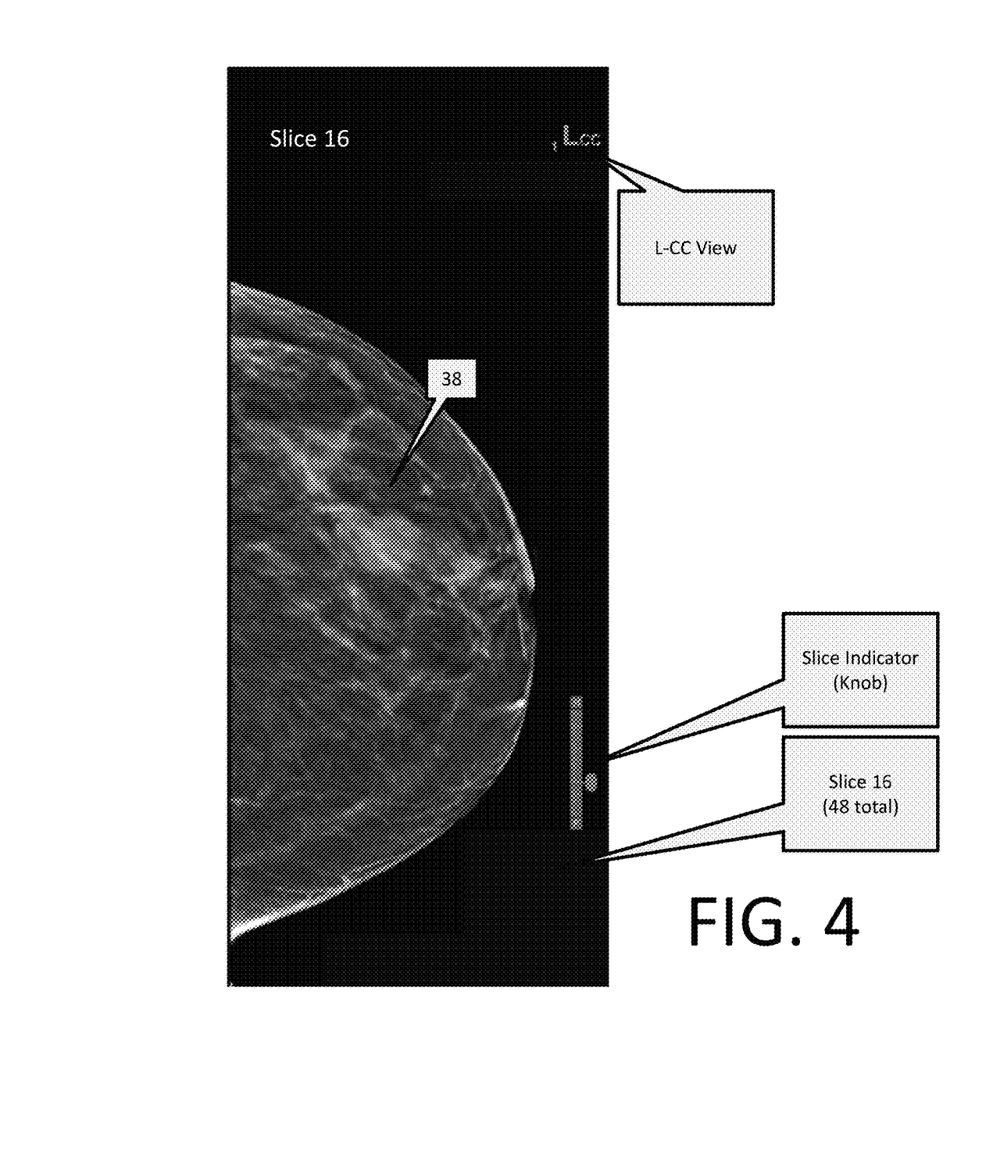
FIG. 4 depicts a single monitor displaying an $L_{CC}$ image slice from the same image set as the $L_{CC}$ image displayed in FIG. 3.
Figure 4A:
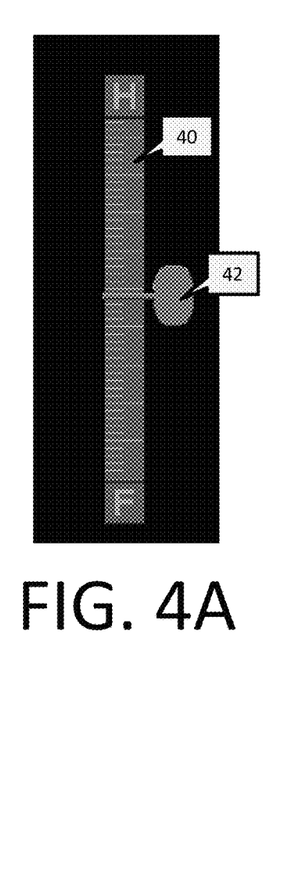
FIG. 4A is a close up view of a slice indicator that is displayed alongside the respective image slices that indicates the slice number of a presently-displayed image slice.

FIG. 4 depicts monitor 34L displaying $L_{CC}$ slice 16 of the same tomo stack as $L_{CC}$ slice 24 displayed in FIG. 3. The round mass 38 is visible in $L_{CC}$ slice 16, but is not as focused as in $L_{CC}$ slice 24 of FIG. 3, indicating that the actual location of the mass along the z-axis of the $L_{CC}$ tomo stack is closer to slice 24 than slice 16. As best seen in FIG. 4A, a slice indicator 40 including an animated "sliding knob" is provided at a lower right-hand corner of each display to provide the reviewer with the slice number (i.e., relative z-axis location) of a presently-displayed slice of a tomo stack. Thus, as the reviewer scrolls through the image slices of a tomo stack using a suitable user interface (i.e., computer mouse), the knob 42 on the slice indicator moves to reflect the currently displayed slice. An audible tone (e.g., a "clicking") may also be provided to indicate to the reviewer that the displayed slice has changes to a next one in the tomo stack.

Figure 5:
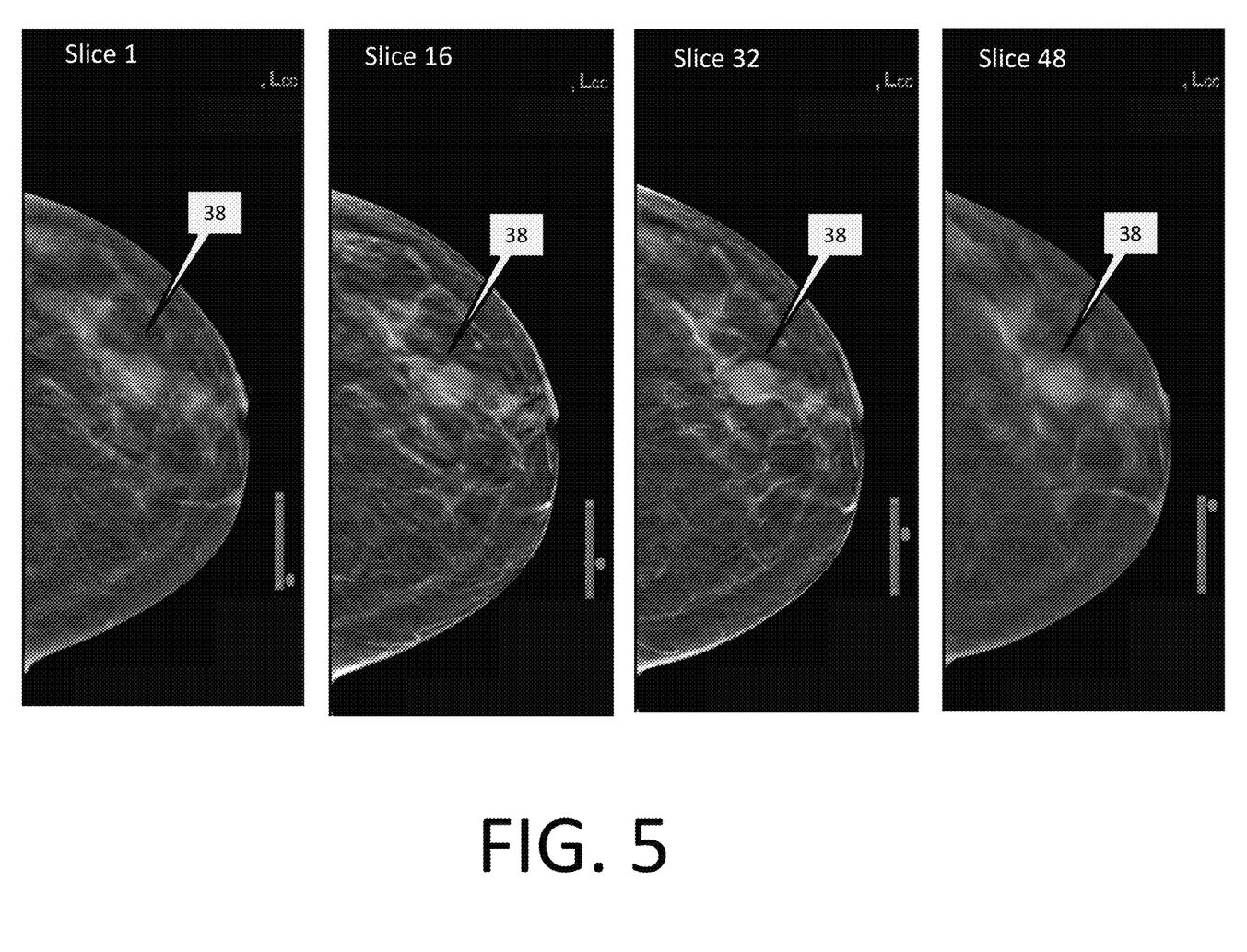
FIG. 5 depicts displayed $L_{CC}$ image slices obtained from the same tomosynthesis image set as the $L_{CC}$ images of FIGS. 3 and 4, illustrating a difference in visibility and clarity of a round tissue mass, depending on a relative z-axis location of the image slice.

In order to provide the perspective of the reviewer, FIG. 5 depicts the respective image slices 1, 16, 32 and 48 of the (same) $L_{CC}$ tomo stack as the images depicted in FIGS. 3 and 4, which clearly illustrate the differences in visibility and clarity of the round mass 38, depending on a relative z-axis location of the respective image slice. In particular, the mass is hard to make out in slice 1, but becomes more visible in slice 16, and is still more visible and clear (in terms of the edges, brightness, etc.) in slice 32, only to become blurred and difficult to make out in slice 48.

Figure 6:
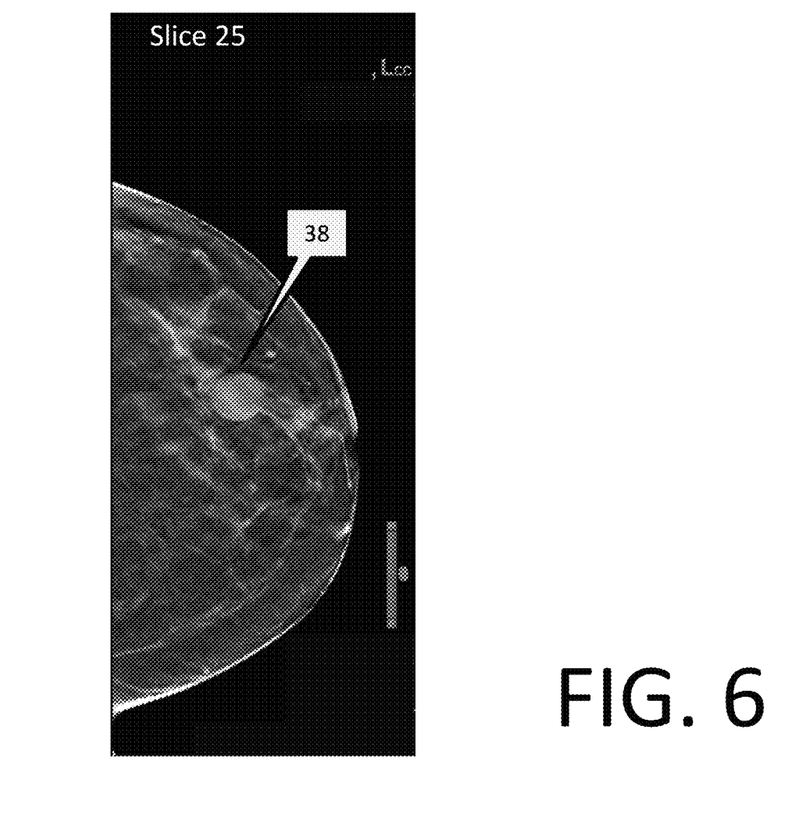
FIG. 6 depicts a displayed best focus $L_{CC}$ slice out of still the same tomosynthesis image set as FIGS. 3-5.

In one embodiment, the system detects through the user interface a user selection or indication of an object or region of interest in a then-displayed image from the tomo stack, and in response, displays an image from the data set having a best focus measure of the user selected or indicated object or region of interest. For example, FIG. 6 depicts a displayed "best focus" $L_{CC}$ image slice (slice 25) out of the (same) tomosynthesis image set with respect to the visibility and clarity of the round tissue mass 38. As explained in greater detail herein, the best focus slice 25 with respect to the tissue mass 38 was determined by the system processer based on a comparison of a computed focus measure of the tissue mass 38 for each image slice 1-48 of the $L_{CC}$ tomo stack. It is, of course, possible that the image slice displayed at the time the reviewer selects or otherwise indicates a particular object or region of interest make in fact turn out to be the image having the best focus of the user selected or indicated object or region of interest. In this case, the image processor may provide a visual or audible signal to the reviewer to indicate same (e.g., a beeping tone and/or highlighting of the object), since the image slice being displayed will not otherwise change.

Figure 7:
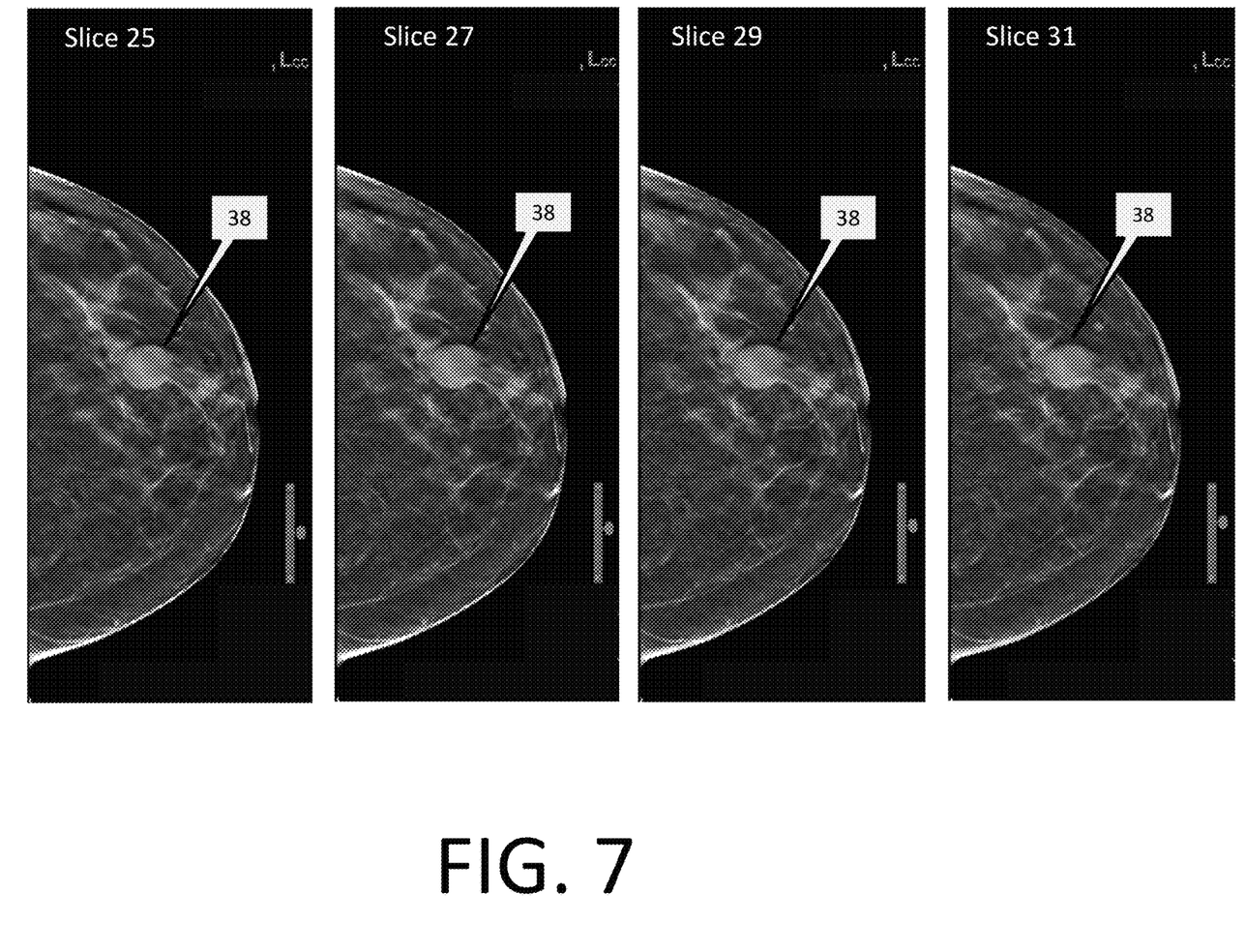
FIG. 7 depicts a series of displayed near-focus $L_{CC}$ slices from the (same) tomosynthesis image set, including the best focus image slice plus subsequent slices along the z-axis.

In another embodiment, the system detects through the user interface a user selection or indication of an object or region of interest in a then-displayed image from the tomo stack, and in response, displays a series of near-focus images from the data set on the display monitor, the series of near focus images comprising images of the data set having computed focus measure values within a predetermined range of, and including, a best focus measure value computed for any image of the data set depicting the user selected or indicated object or region of interest. For example, FIG. 7 depicts a series of displayed near-focus $L_{CC}$ image slices from the (same) tomosynthesis image set, including the best focus $L_{CC}$ slice 25, plus subsequent $L_{CC}$ slices 27, 29 and 31, demonstrating slight changes in visibility and clarity of the round tissue mass 38 as the respective image slices progress along the z-axis from the best-focused slice 25 (far left displayed image) to the relatively least-focused slice 31 (far right displayed image).

Figure 9:
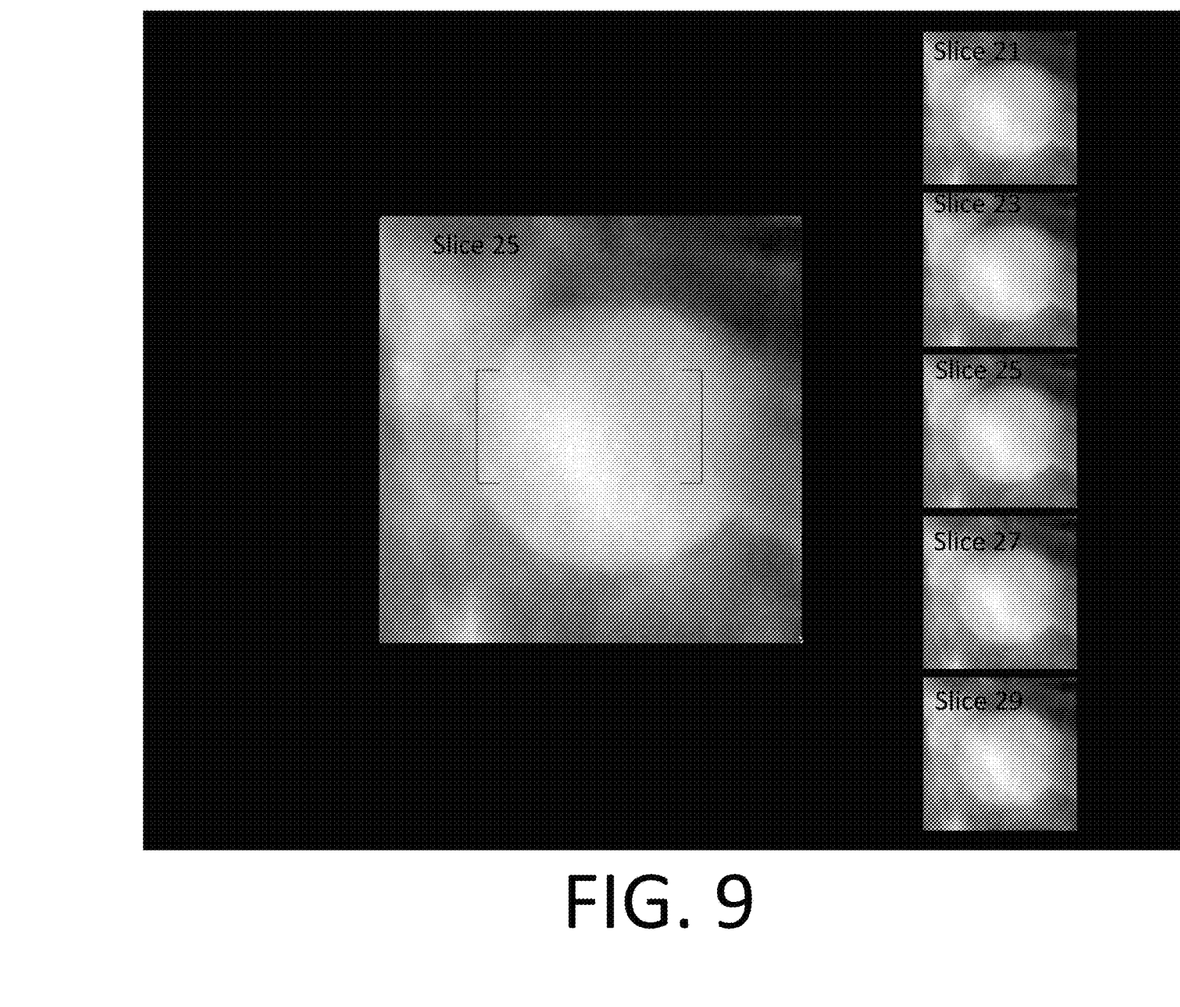
FIG. 9 depicts the displayed best focus $L_{CC}$ slice in a center area of the monitor, with the series of near-focus $L_{CC}$ slices displayed in a stacked formation alongside the best focus slice.

In one embodiment, such as depicted in FIG. 9, the series of near-focus images are displayed simultaneously, so as to allow for a static review and comparison of the user selected or indicated object or region of interest in each image of the near-focus series. In particular, FIG. 9 depicts the best focus $L_{CC}$ image slice 25 displayed in a center area of the monitor, with the subset near-focus $L_{CC}$ image slices 21, 23, 25, 27 and 29 displayed in a stacked formation alongside the best focus image slice 25 to allow the reviewer to see the changes in the tissue mass in each direction along the z-axis from slice 25.

In another embodiment, the series of near-focus of images are displayed in succession, so as to allow for a dynamic review and comparison of the user selected or indicated object or region of interest in each image of the near-focus series. For example, the images slices 25, 27, 29 and 31 of FIG. 7 may be automatically displayed in consecutive order, one at a time, and each for a predetermined amount of time (e.g., 1 second) in order to convey to the reviewer the changes in the object or region of interest along the z-axis of the tomo stack. This "video loop" functionality may be optionally configured to be repeated multiple times, and further optionally with the respective images slices displayed in a different order (e.g., lowest slice to highest, then reverse order) during different loop sequences. Preferably, specific parameters for displaying the images of a series of near-focus images is configurable through the user interface.

In some embodiments, in order to assist the reviewer, the system employs known image processing techniques to identify different breast tissue objects and structures in the various source images, and the reviewer may (optionally) cause the system to highlight such objects and structures in the respective best focus image and/or near-focus images, in particular, tissue structures comprising or related to abnormal objects, such as micro-calcification clusters, round-or-lobulated masses, spiculated masses, architectural distortions, etc.; as well as benign tissue structures comprising or related to normal breast tissues, such as linear tissues, cysts, lymph nodes, blood vessels, etc. For example, a user selected or indicated object or region of interest is highlighted by a contour line representing a boundary of the highlighted object or region. Furthermore, objects or regions of interest consisting of or including differing types of tissue structures may be highlighted in different manners when they are a respective subject of a focusing process.

Figure 8:
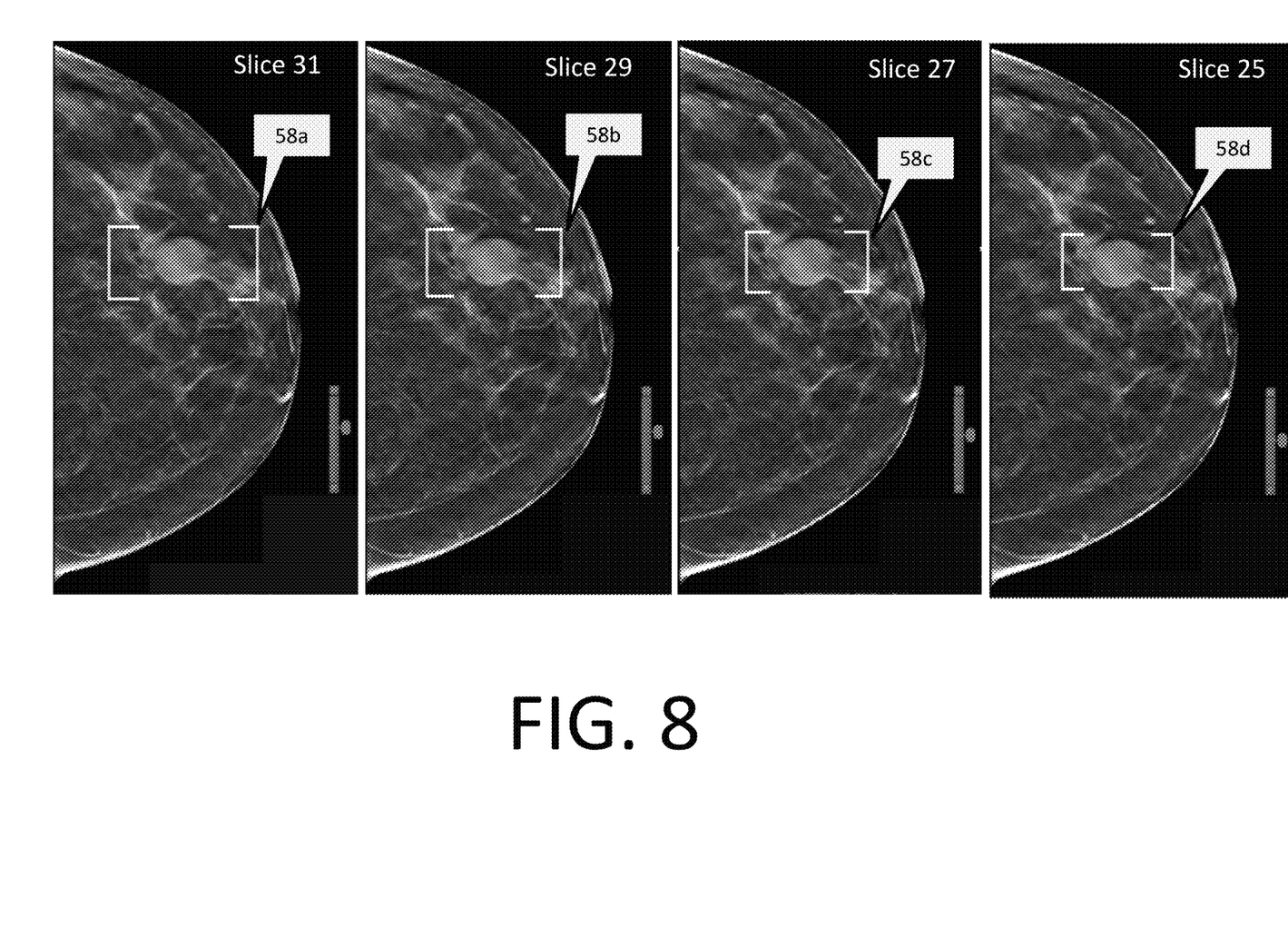
FIG. 8 depicts the series of displayed near-focus $L_{CC}$ image slices shown in FIG. 7, but in reverse order, wherein the round mass is highlighted with a visual indicia in the form of rectangular brackets.

By way of non-limiting illustration, FIG. 8 depicts the series of displayed near-focus $L_{CC}$ image slices shown in FIG. 7, but in reverse order, i.e., slices 31, 29, 27 and 25. wherein the round mass is highlighted with a visual indicia in the form of rectangular brackets 58a-d, which move progressively closer around the tissue mass 38, as the image slices progress along the z-axis from the relatively least-focused slice 31 (far left image) to best-focused slice 25 (far right image). Again, the presentation of the respective images slices of the series of near-focus images may be presented at the same time (for a static comparison), or in a video-loop style format, for a dynamic comparison.

Figure 10:
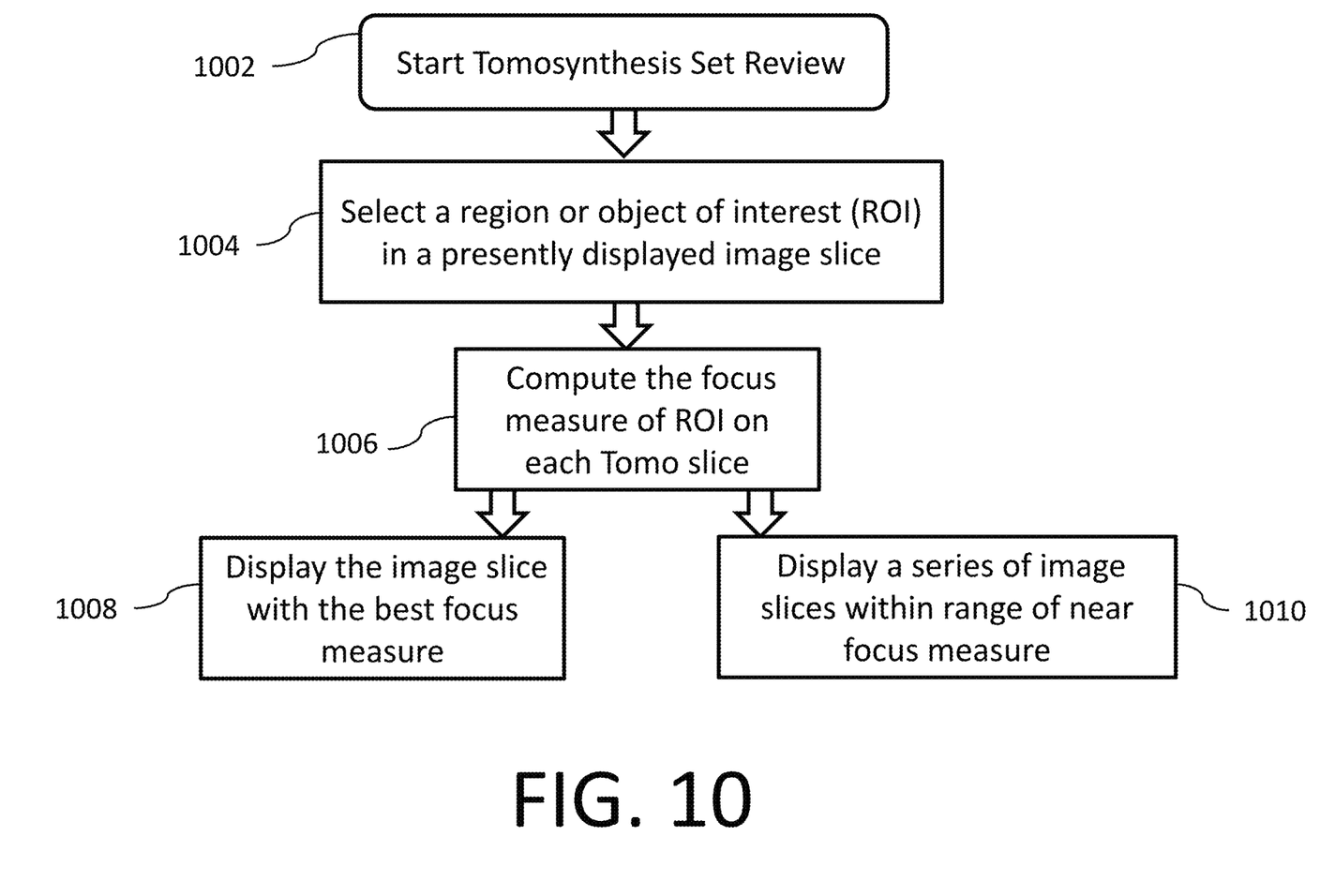
FIG. 10 is a flow diagram illustrating an exemplary process for displaying a best focus image slice or a series of near-focus slices of an object or region of interest in a tomosynthesis image set.

FIG. 10 is a flow diagram illustrating an exemplary process for displaying an image slice from a tomosynthesis data set having a best focus measure of a user selected or indicated object or region of interest in a previously displayed image slice from the set. Initially, at step 1002, the reviewer causes the system to initiate review of a tomosynthesis image set, e.g., of the prior illustrated and described $L_{CC}$ tomo stack having 48 slices. Thereafter, the reviewer scrolls through the image slices, typically but necessarily in an ascending order beginning at slice 1.

At step 1004, the reviewer selects or otherwise indicates an interest (i.e., for clinical evaluation) in an object or region of tissue in a then-displayed image slice of the tomo stack. Upon detecting the user selection or indication of an object or region of interest (hereinafter collectively referred to as "ROI" for purposes of describing the processes in FIGS. 10 and 11), at step 1006, the system thereafter computes a focus measure for the selected/indicated ROI in each image slice of the tomo stack.

As explained in greater detail below in conjunction with FIGS. 11 and 12, depending on the desired display protocol indicated by the reviewer, at step 1008, the system displays the image slice from the tomo stack having a best, (e.g., "highest" depending on the measuring protocol) focus measure out of all image slices of the tomo stack for the ROI. Alternatively or additionally, at step 1010, the system may display a series of near-focus image slices of the ROI, as described above. The range of slices that fall into a near-focus series may be pre-configured by the system, or user configurable. For example, a user may indicate through the user interface that the displayed series is include a selected number of images (e.g., five) out of the tomo stack having focus measures within a range of the five percent of one another and including the image having the best focus measure.

Figure 11:
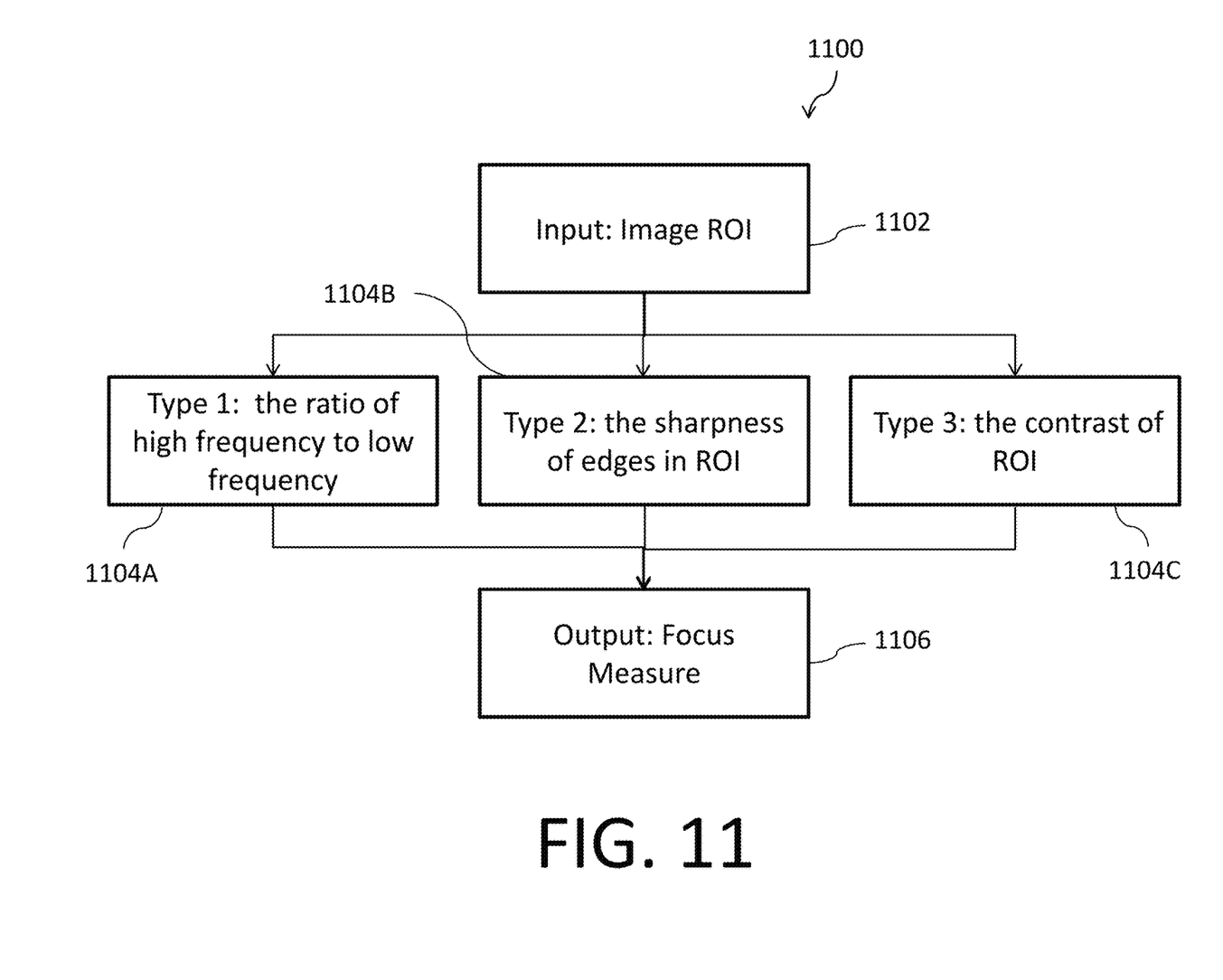
FIG. 11 is a flow diagram illustrating exemplary processes for computing a focus measure of an object or region of interest in a tomosynthesis image set.
Figure 12:
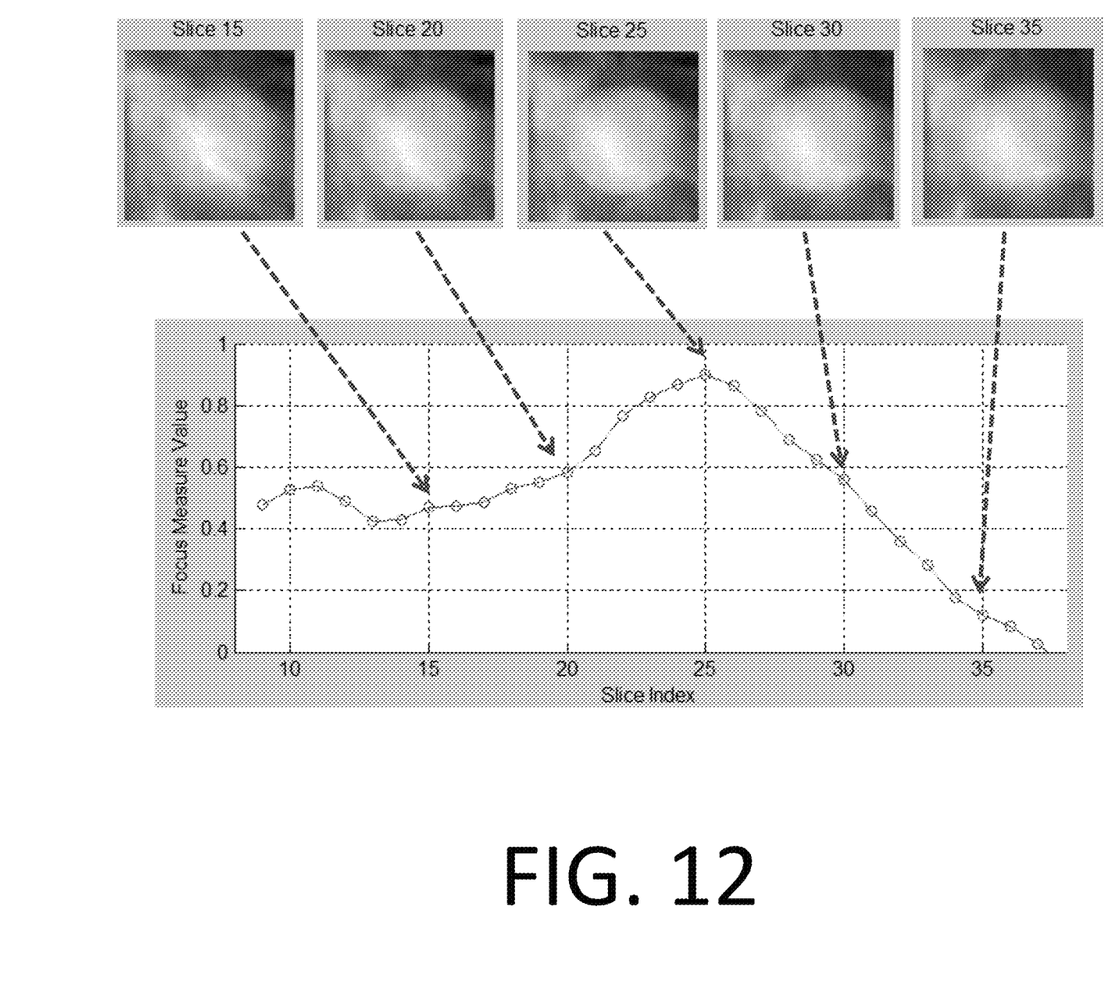
FIG. 12 illustrates a process for identifying an image having a highest relative focus measure of all images in a tomosynthesis image set with respective to a selected object or region of interest.

FIG. 11 is a flow diagram 1100 illustrating exemplary processes for computing a focus measure of a user selected or indicated object or region of interest in a displayed image slice of a tomosynthesis image set. As discussed above, the process begins, at step 1102, upon the reviewer selecting or otherwise indicating an ROI in a presently displayed (or "then-displayed") image slice. The image slice having a best focus measure of the ROI out of the entire tomo stack is then determined by the system based on a comparison of a focus measure of the ROI for each image slice of the tomo stack.

In accordance with the presently disclosed inventions, a determination of focus score and, thus, a best focus score, may be accomplished in a number of ways including, at step 1104A, wherein the focus measure is computed according to known image processing techniques based on a sharpness of detected edges of the object or region of interest. For example, the total gradient magnitude of detected edges inside region of interest is a known measure for sharpness of detected edges. Alternatively and/or additionally, at step 1104B, the focus measure may be computed according to known image processing techniques based on a computed contrast of the object or region of interest, wherein the contrast can be defined as the absolute difference of a pixel with its eight neighbors, summed over all the pixels in region of interest. Alternatively and/or additionally, at step 1104C, the focus measure may be computed according to known image processing techniques based on a ratio between a measured magnitude of one or more high frequency components and a measured magnitude of one or more low frequency components, wherein high frequency components correspond to sharp edges of the object in the foreground, while low frequency components correspond to a blur area in the background. A high value of the ratio between a measured magnitude of high frequency components and a measured magnitude of low frequency components indicates that the object or region of interest is in focus.

Once the focus measure for each slice has been determined, at step 1106, the system may cause to be displayed the image slice having the best focus measure score and/or a series of images having focus measures within a predetermined range, e.g., within 5% of the best focus measure. This process is illustrated for the above-described and illustrated $L_{CC}$ tomo stack in FIG. 12, which depicts for purposes of illustration respective computed focus measure values of the round tissue mass 38 for images slices 15, 20, 25, 30 and 35, progressing along the z-axis of the $L_{CC}$ tomo image stack. In particular, the focus measure scores plotted in the graph of FIG. 12 were computed using a ratio between the measured magnitude of high frequency components and the measured magnitude of low frequency components within the selected image ROI. As can be seen, image slice 25 has the highest focus measure value, which in this case also means the "best" focus measure.

Having described exemplary embodiments, it can be appreciated that the examples described above and depicted in the accompanying figures are only illustrative, and that other embodiments and examples also are encompassed within the scope of the appended claims. For example, while the flow diagrams provided in the accompanying figures are illustrative of exemplary steps; the overall image merge process may be achieved in a variety of manners using other data merge methods known in the art. The system block diagrams are similarly representative only, illustrating functional delineations that are not to be viewed as limiting requirements of the disclosed inventions. Thus the above specific embodiments are illustrative, and many variations can be introduced on these embodiments without departing from the scope of the appended claims.

The invention claimed is:

1. An automated method employing a computer-controlled workstation for navigating and displaying breast tissue images, the workstation comprising an operatively associated user interface and display monitor, the method comprising:
    obtaining a tomosynthesis image data set, the data set comprising volumetric image data of a breast;
    displaying an image or a series of images from the data set on the display monitor in response to one or more user commands received through the user interface;
    detecting through the user interface a user selection or indication of an object or region of interest in a then-displayed image from the data set; and
    displaying an image from the data set having a best focus measure of the user selected or indicated object or region of interest, wherein the image having the best focus measure is determined by computing a respective focus measure of the object or region of interest computed for each image of the data set, and then comparing the computed focus measures, wherein displaying an image from the data set having a best focus measure of the user selected or indicated object or region of interest comprises displaying a series of near-focus images from the data set on the display monitor, the series of near focus images comprising images of the data set having computed focus measure values within a predetermined range.

2. The method of claim 1, wherein the series of near-focus images are displayed simultaneously, so as to allow for a static review and comparison of the user selected or indicated object or region of interest in each image.

3. The method of claim 1, wherein the images of the series of near-focus images are displayed in succession, so as to allow for a dynamic review and comparison of the user selected or indicated object or region of interest in each image.

4. The method of claim 1, wherein parameters for the selection and displaying of the series of near-focus images are configurable through the user interface.

* * * * *